(12) United States Patent
Markert et al.

(10) Patent No.: US 6,867,175 B2
(45) Date of Patent: Mar. 15, 2005

(54) TRIMETHYLDECENYL COMPOUNDS

(75) Inventors: Thomas Markert, Monheim (DE); Theo Ten Pierik, Venlo (NL); Werner Faber, Willich (DE)

(73) Assignee: Kao Corporation, Tokyo (JP)

( * ) Notice: Subject to any disclaimer, the term of this patent is extended or adjusted under 35 U.S.C. 154(b) by 35 days.

(21) Appl. No.: 10/275,724

(22) PCT Filed: Apr. 28, 2001

(86) PCT No.: PCT/EP01/04817

§ 371 (c)(1),
(2), (4) Date: Apr. 15, 2003

(87) PCT Pub. No.: WO01/85672

PCT Pub. Date: Nov. 15, 2001

(65) Prior Publication Data

US 2003/0153485 A1 Aug. 14, 2003

(30) Foreign Application Priority Data

May 6, 2000 (DE) .......................... 100 22 076

(51) Int. Cl.⁷ ................................. A61K 7/46
(52) U.S. Cl. .............. 512/6; 512/25; 512/27; 558/303; 558/435; 568/420; 568/448; 568/700; 568/840; 568/909.5; 568/924; 568/943

(58) Field of Search .............. 512/6, 25, 27; 558/303, 435; 568/420, 448, 700, 840, 909.5, 924, 943

(56) References Cited

U.S. PATENT DOCUMENTS 4,579,680 A * 4/1986 Sell ............................ 512/6

* cited by examiner

Primary Examiner—Monique T. Cole
(74) Attorney, Agent, or Firm—Oblon, Spivak, McClelland, Maier & Neustadt, P.C.

(57) ABSTRACT

A Compound corresponding to formula (I):

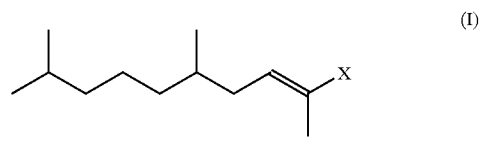

wherein X is a group selected from the group consisting of —CHO, —CN, —CH=NOH, and —CH₂OH, and wherein the C=C double bond assumes a Z or E configuration.

4 Claims, No Drawings

TRIMETHYLDECENYL COMPOUNDS

BACKGROUND OF THE INVENTION

This application is a 371 of PCT/EP01/04817 filed Apr. 28, 2001.

This invention relates to new trimethyldecene compounds with a special structure and to their use as perfumes.

Judging by demand, many natural perfumes are available in totally inadequate quantities. For example, 5,000 kg of rose blossoms are required to produce 1 kg of rose oil. The consequences are extremely limited annual world production and a high price. Accordingly, it is clear that there is a constant need in the perfume industry for new perfumes with interesting fragrance notes. On the one hand, the range of naturally available perfumes can be extended in this way; on the other hand, it is thus possible to make the necessary adaptations to changing fashion trends. In addition, it is possible in this way to meet the steadily increasing demand for odor enhancers for products of everyday use, such as cosmetics and cleaners.

In addition, there is generally a constant need for synthetic perfumes which can be favorably produced in a consistent quality and which have desirable olfactory properties, i.e. in particular pleasant, near-natural and qualitatively new odor profiles of adequate intensity, and which are capable of advantageously influencing the fragrance of cosmetic and consumer products. In other words, there is a constant need for compounds which have characteristic new odor profiles coupled with high staying power, intensity of odor and emanative power.

DESCRIPTION OF THE INVENTION

It has been found that the compounds corresponding to general formula (I) excellently satisfy the above-mentioned requirements in every respect and may advantageously be used as perfumes with differently nuanced perfume notes characterized by high staying power.

In a first embodiment, the present invention relates to trimethyldecene compounds corresponding to general formula (I):

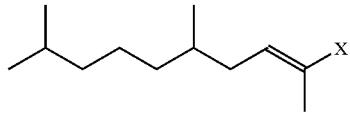

(I)

in which X is a —CHO or —CN or —CN=NOH or —CH$_2$OH group, the C=C double bond assuming the Z or E configuration.

In another embodiment, the present invention relates to the use of trimethyldecene compounds corresponding to general formula (I) above as perfumes.

The compounds (I) according to the invention are distinguished by an odor characteristic in which mandarin notes and fruity aspects dominate. They show excellent stability in cosmetic and consumer perfumery formulations.

The compounds (I) may be prepared by known synthesis processes of organic chemistry.

In perfume compositions, the compounds (I) strengthen harmony, emanation, naturalness and also staying power, the quantities used being adapted to the particular perfume note required taking the other ingredients of the composition into account.

The fact that the compounds (I) have the above-mentioned perfume notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

By virtue of their odor profile, the compounds corresponding to formula (I) are also particularly suitable for modifying and enhancing known compositions. Particular emphasis is placed on their extreme intensity of odor which contributes quite generally towards refining the composition.

The compounds corresponding to formula (I) may be combined with many known perfume ingredients, for example other perfumes of natural, synthetic or partly synthetic origin, essential oils and plant extracts. The range of natural fragrances can thus include both high-volatility and also medium-volatility and low-volatility components while the range of synthetic perfumes may include representatives of virtually every class of compounds.

Examples of suitable substances with which the compounds (I) may be combined are, in particular, (a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil (b) alcohols, such as farnesol, geraniol, linalool, nerol, phenylethyl alcohol, rhodinol, cinnamic alcohol, sandalore [3-methyl-5-(2,2,3-trimethylcyclopent-3-en-1-yl)-pentan-2-ol], sandela [3-isocamphyl-(5)-cyclohexanol]

(c) aldehydes, such as citral, Helional®, α-hexyl cinnamaldehyde, hydroxycitronellal, Lilial® [p-tert.butyl-α-methyldihydrocinnamaldehyde], methylnonyl acetaldehyde (d) ketones, such as allylionone, α-ionone, β-ionone, isoraldein, methyl ionone (e) esters, such as allylphenoxyacetate, benzyl salicylate, cinnamyl propionate, citronellyl acetate, decyl acetate, dimethylbenzyl carbinyl acetate, ethyl acetoacetate, hexenyl isobutyrate, linalyl acetate, methyl dihydrojasmonate, vetiveryl acetate, cyclohexyl salicylate (f) lactones, such as gamma-undecalactone, 1-oxaspiro[4.4]-nonan-2-one and various other components often used in perfumery, such as musk and sandalwood perfumes, indole, p-methan-8-thiol-3-one, methyl eugenol, Ambroxan.

It is also remarkable how the compounds corresponding to formula (I) round off and harmonize the odor notes of a broad range of known compositions without unpleasantly dominating them in any way. 2,5,9-Trimethyldec-2-ene nitrile is particularly emphasized in this regard.

The compounds according to the invention or mixtures thereof may be used in perfume compositions in quantities of 1 to 70% by weight, based on the mixture as a whole. Mixtures of compounds (I) according to the invention and compositions of this type may be used both for perfuming cosmetic preparations, such as lotions, creams, shampoos, soaps, emollients, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming these various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

EXAMPLES

Example 1

Preparation of 2,5,9-trimethyldec-2-enal
Materials:
a) 156 g (1 mol) 3,6-dimethyl octanal
b) 174 g (3 mol) propanal
3) 4.2 g (0.05 mol) piperidine
4) 3.0 g (0.05 mol) acetic acid
5) 200 ml toluene
Apparatus:
1-liter three-necked flask with stirrer, thermometer and water separator
Method:
Components 1), 2) and 5) were successively weighed into the flask with stirring. Component 3) was then added to the mixture with stirring at room temperature, followed by component 4). The mixture was heated under reflux for 4 hours on a water separator while the water of reaction was distilled off and 25 ml of water were drained off. Monitoring of the conversion indicated a product concentration of 57.3%. After the addition of more of components 3) and 4) and heating under reflux for 2 hours, 33 ml of water had separated off and the product concentration amounted to 82.4%. The reaction mixture was cooled and washed twice with 10% sodium sulfate solution in a separation funnel, dried over $MgSO_4$, concentrated in a rotary evaporator and the residue of 202 g of a yellow liquid was used for distillation in a 30 cm packed column. 145 g of main fraction with a gas chromatographic (GC) purity of 95% were obtained at 70–75° C./0.06 mbar.
Yield:
69.5% of the theoretical
The IR spectrum (film between NaCl) showed characteristic vibration bands at 1690 (CO) and 2709 $cm^{-1}$. The $^1$H-NMR showed signals for 2 methyl groups (doublets) at 0.9 ppm and 1 methyl group at 1.7 ppm, several multiplets at 1.2 and 1.5 ppm (4 $CH_2$ groups) besides 2 septets (per 1 H) at 2.2 and 2.3 ppm and one doublet of the triplet at 6.5 ppm (1 olefinic H). The aldehyde proton produced a singlet at 9.4 ppm.
Odor:
Initial perfume of orange, mandarin, MNA (MNA=methyl nonyl acetaldehyde), after-perfume of orange.

Example 2

Preparation of 2,5,9-trimethyldec-2-enal oxime
Materials:
1) 60.8 g (0.375 mol) hydroxylamine sulfate in 240 ml water
2) 24.0 g (0.6 mol) sodium hydroxide in 48 ml water
3) 121.7 g 2,5,9-trimethylden-2-enal (96%) prepared as described in Example 1.
Apparatus:
2-liter four-necked flask with stirrer and dropping funnel.
Method:
Component 1) was introduced into the flask first and component 2) was then added dropwise with stirring over 20 minutes, the temperature rising from 17 to 25° C. Component 3) was added over a period of 30 minutes with stirring and cooling. Thereafter the mixture was pale yellow in color. The reaction mixture was heated to 80° C. and stirred at that temperature for 1 hour. After 1 hour, the concentration of the product was 86.7%, that of the educt 11.2%. After 2 hours: 88.8% product and 8.3% educt.
Working Up:
The mixture was cooled and extracted twice with 100 ml of ether, the ether phases were washed with water and sodium sulfate solution (pH 6) and dried overnight with sodium sulfate. The solvent was concentrated in a rotary evaporator and 113.17 g of product with a content of 84.9% were obtained as residue. The crude product was distilled in a 15 cm Vigreux column. 99 g of orange-colored main fraction with a GC purity of 94% were obtained at 119–136° C./0.15–0.12 mbar.
Yield:
66.5% of the theoretical.
Odor Characteristic:
Initial perfume metallic, wet hide, orange, mandarin; after-perfume of mandarin.

Example 3

Preparation of 2,5,9-trimethyldec-2-ene nitrile
Materials:
1) 91 g (0.41 mol) of 2,5,9-trimethyldec-2-enal oxime (94%) prepared as described in Example 2
2) 109.24 g (1.07 mol) acetanhydride.
Apparatus:
Two-liter four-necked flask with stirrer, PT 100 thermometer, 250 ml dropping funnel and reflux condenser, ice water bath for cooling, oil bath for heating.
Method:
Component 1) was introduced into the reaction vessel first and component 2) was then added dropwise with stirring and cooling over a period of 30 minutes. The temperature of the mixture rose from 22° C. to 33° C. After addition of 28 g of the acetanhydride, there was a change in color, the originally orange-colored mixture becoming lighter. After 2) has been completely added, the temperature was increased to 130° C. and the mixture was stirred at that temperature for 1 hour.
Working Up:
The reaction mixture was poured onto 300 g of ice, the organic phase was removed and the aqueous phase was extracted three times with 100 ml of ether. The organic phases were combined and neutralized with sodium bicarbonate. The neutralizate was dried over sodium sulfate and concentrated in a rotary evaporator. 91.1 g of crude product (92.3% peak area) were obtained. The crude product was distilled in a 15 cm Vigreux column, 59.2 g of main fraction passing over at 79–80° C./0.08–0.06 mbar. The GC purity was 98.6%.
Yield:
86.4% of the theoretical.
Analysis:
The IR spectrum (film between NaCl) showed characteristic vibration bands at 1461 (C=C) and 2218 (CN) $cm^{-1}$. The $^1$H-NMR showed signals for 2 methyl groups (doublets) at 0.9 ppm and a singlet for a methyl group at 1.9 ppm. The four $CH_2$ groups give multiplets at 1.1, 1.3, 1.5 and 1.6 ppm. Two multiplets for the two Hs at C-5 and C-9 appeared at 2.0 and 2.1 ppm. The olefinic H appeared as a doublet of the triplets at 6.4 ppm.
Odor Characteristic:
Initial perfume of tridecene-2-nitrile, mandarin, wet hide, metallic; after-perfume of nitrile, mandarin.

What is claimed is:

1. A compound corresponding to formula (I):

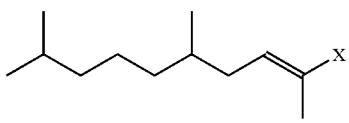
(I)

wherein X is a group selected from the group consisting of —CHO, —CN, —CN=NOH, and —CH₂OH, and wherein the C=C double bond assumes a Z or E configuration.

2. A composition comprising a compound corresponding to formula (I):

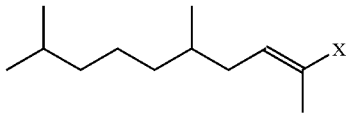
(I)

wherein X is a group selected from the group consisting of —CHO, —CN, —CN=NOH, and —CH₂OH, and wherein the C=C double bond assumes a Z or E configuration.

3. The composition of claim 2 wherein the compound is present in the composition in an amount of from about 1 to 70% by weight, based on the weight of the composition.

4. A process for imparting fragrance onto a substrate comprising contacting the substrate with a compound corresponding to formula (I):

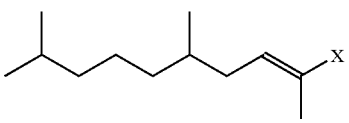
(I)

wherein X is a group selected from the group consisting of —CHO, —CN, —CN=NOH, and —CH₂OH, and wherein the C=C double bond assumes a Z or E configuration.

* * * * *

UNITED STATES PATENT AND TRADEMARK OFFICE
CERTIFICATE OF CORRECTION

PATENT NO. : 6,867,175 B2
DATED : March 15, 2005
INVENTOR(S) : Thomas Markert et al.

It is certified that error appears in the above-identified patent and that said Letters Patent is hereby corrected as shown below:

<u>Title page,</u>
Item [75], Inventors, replace "Theo, Ten Pierik, Venlo (NL)" with -- Theo, Ten Pierik, LE Venlo (NL) --.

<u>Column 5,</u>
Line 12, replace "whereir", with -- wherein --.

Signed and Sealed this

Seventh Day of June, 2005

JON W. DUDAS
*Director of the United States Patent and Trademark Office*